(12) United States Patent
Kram et al.

(10) Patent No.: US 6,208,940 B1
(45) Date of Patent: Mar. 27, 2001

(54) CONE TIPPED CYLINDRICAL PROBE FOR USE IN GROUNDWATER TESTING

(75) Inventors: Mark L. Kram, Santa Barbara; James A. Massey, Ventura, both of CA (US)

(73) Assignee: The United States of America as represented by the Secretary of the Navy, Washington, DC (US)

(*) Notice: Subject to any disclaimer, the term of this patent is extended or adjusted under 35 U.S.C. 154(b) by 0 days.

(21) Appl. No.: 09/111,629

(22) Filed: Jun. 25, 1998

Related U.S. Application Data (63) Continuation-in-part of application No. 09/054,290, filed on Mar. 30, 1998.

(51) Int. Cl.⁷ .......................... G01N 11/00; G01N 33/24; G01N 15/08; G01N 3/00
(52) U.S. Cl. .................... 702/12; 702/11; 702/2; 73/38; 73/84
(58) Field of Search ............ 73/84, 38, 152.41, 73/73; 702/11, 12, 2

(56) References Cited

U.S. PATENT DOCUMENTS

| | | | |
|---|---|---|---|
| 4,442,701 | * 4/1984 | Cowherd et al. | 73/32 |
| 4,806,153 | * 2/1989 | Sakai et al. | 73/84 |
| 4,969,111 | * 11/1990 | Merva | 73/73 |
| 5,042,595 | 8/1991 | Ladanyi | 175/50 |
| 5,109,702 | 5/1992 | Charlie et al. | 73/84 |
| 5,316,950 | * 5/1994 | Apitz | 73/84 |
| 5,377,551 | * 1/1995 | Vacquer | 73/84 |
| 5,616,833 | 4/1997 | Anderson | 73/84 |

* cited by examiner

Primary Examiner—Hazron Williams
Assistant Examiner—Katina Wilson
(74) Attorney, Agent, or Firm—David Kalmbaugh

(57) ABSTRACT

A piezocone for measuring the soil's resistance to penetration and pore water pressure while being advanced into the ground by a rig. The piezocone includes a friction sleeve and a conical tip attached to the lower end of the sleeve. The conical tip develops the cone resistance. The friction sleeve is an isolated cylindrical sleeve which measures the resistance of the soil as the sleeve passes through the soil. The pore water pressure is measured by a porous element mounted in the conical tip of the piezocone and a pressure transducer mounted in the cylindrical friction sleeve of the piezocone. The measurements including pore water pressure, cone resistance and soil resistance are supplied to a computer which includes a Piezocone Dissipation Analysis program for processing data from the measurements to generate dissipation curves for each depth at which the piezocone provides hydrogeologic site characterization data. Soil classification is also provided from a data file stored within the computer. The Piezocone Dissipation Analysis program generates a Hydrostatic Pressure Profile curve and a Hydraulic Conductivity Profile Plot. A water depth below surface estimate is provided using the Hydrostatic Pressure Profile curve zero pressure intercept. The Hydraulic Conductivity Profile Plot may be generated using coefficients of Permeability from a soil classification table.

13 Claims, 8 Drawing Sheets

CONE TIPPED CYLINDRICAL PROBE FOR USE IN GROUNDWATER TESTING

This application is a continuation-in-part of U.S. patent application Ser. No. 09/054,290, filed Mar. 30, 1998. A computer program listing related to this invention is included in a microfiche appendix on one microfiche having a total of 98 frames pursuant to 37 CFR 1.96(b).

BACKGROUND OF THE INVENTION

1. Field of the Invention

The present invention relates generally to an apparatus and method for ground water testing. More specifically, the present invention relates to a cone tipped cylindrical probe and a computer software program adapted for use with the probe which provides an effective means of pore pressure measurements which can be converted into values for water table evaluation for accessing environmental site conditions.

2. Description of the Prior Art

The cone penetration test was originally developed to measure in-situ soil properties for the design of deep foundations. The electric version of the cone penetration test was introduced commercially in the nineteen seventies primarily as a geotechnical exploration tool. More recently, the cone penetration test range of applications has been extended to environmental site investigations.

The electric cone penetration test is currently being used as an effective means of hydrogeologic site characterization and subsurface plume tracking. An electric cone penetration test probe or piezocone measures pore water pressure and soil resistance to penetration while being advanced into the ground by an approximately 20-ton hydraulic cone penetrometer rig.

Computer processing of the piezocone measurements generally provides detailed stratigraphic profiles which depict depths of water bearing formations and variations in permeability. This data may then be used to determine the optimum depths at which to conduct ground water sampling for plume delineation; to determine direction and gradient of subsurface water flow; to check for aquifer communication and for monitoring of remediation efforts.

The piezocone has several advantages over conventional cone penetration testing methods and apparatus including: (1) the ability to distinguish between drained, partially drained and undrained soils; (2) the ability to correct measured cone data to account for unbalanced water forces due to unequal end areas in cone design; (3) the ability to evaluate flow and consolidation characteristics; (4) the ability to assess equilibrium groundwater conditions; (5) improved soil profiling and identification; and (6) improved evaluation of geotechnical parameters.

While there are a number of commercially available piezocones which may be used for hydrogeologic site characterization and subsurface plume tracking there is a need for a piezocone which will provide very accurate pore pressure measurements. In particular, the piezocone should be able to provide precise values of pore pressure having a total error of less than 0.9 inches of water.

SUMMARY OF THE INVENTION

The present invention overcomes some of the disadvantages of the prior art including those mentioned above in that it comprises a relatively simple yet highly effective electric cone penetration test probe and a computer software program for use with the probe which provides precise values of pore pressure which may then be used for hydrogeologic site characterization.

The electric cone penetration test unit probe of the it$i present invention or piezocone measures the soil's resistance to penetration and pore water pressure while being advanced into the ground be a twenty ton hydraulic cone penetrometer rig.

During a push operation utilizing piezocones, a high pressure piezocone of about 250 psi full scale output or higher is generally used for the first push since zones in the ground are typically aquitards. This first push allows the user of the high pressure piezocone to identify course grained zone/material and fine grained zone/material in the ground. During a second push, a low pressure, high pressure piezocone with approximately a 25 psi full scale output is used to evaluate water levels by measuring pressures in course grained materials. Measurement of pore pressures in coarse grained materials typically takes less time than fine grain materials since equilibrium is established rapidly during dissipation in coarse grained materials.

The low pressure piezocone includes a friction sleeve and a conical tip attached to the lower end of friction sleeve. 1::u The conical tip has an end bearing component of penetration developed thereon. Cone resistance $q_c$, which is the end bearing component of penetration resistance, is measured by a load cell within the piezocone. The friction sleeve is an isolated cylindrical sleeve which measures the resistance of the soil as the sleeve passes through the soil. The pore water pressure is measured by a porous element mounted in the conical tip of the piezocone and a pressure transducer mounted within the piezocone behind the conical tip.

The low pressure piezocone measurements including pore water pressure, cone resistance q, and the soil resistance are supplied to a computer which includes a Piezocone Dissipation Analysis program for processing the piezocone measurements to generate dissipation curves for each depth at which the piezocone provides hydrogeologic site characterization data. Soil classification is also provided from a data file stored within the computer.

The computer uses the Piezocone Dissipation Analysis program to generate a Hydrostatic Pressure Profile curve and a Hydraulic conductivity Profile Plot. The computer also uses the Piezocone Dissipation Analysis program to provide a water depth below surface estimate which occurs at the Hydrostatic Pressure Profile curve zero pressure intercept.

The computer's Piezocone Dissipation Analysis program My includes a file allowing the user to select an option which includes a CPT (cone penetration test) soil classification table having coefficients of permeability which are fixed value coefficients for each soil type encountered during a push operation. The Hydraulic Conductivity Profile is then is, generated using the coefficients of permeability from this table.

DETAILED DESCRIPTION OF THE PREFERRED EMBODIMENT

Figure 1:
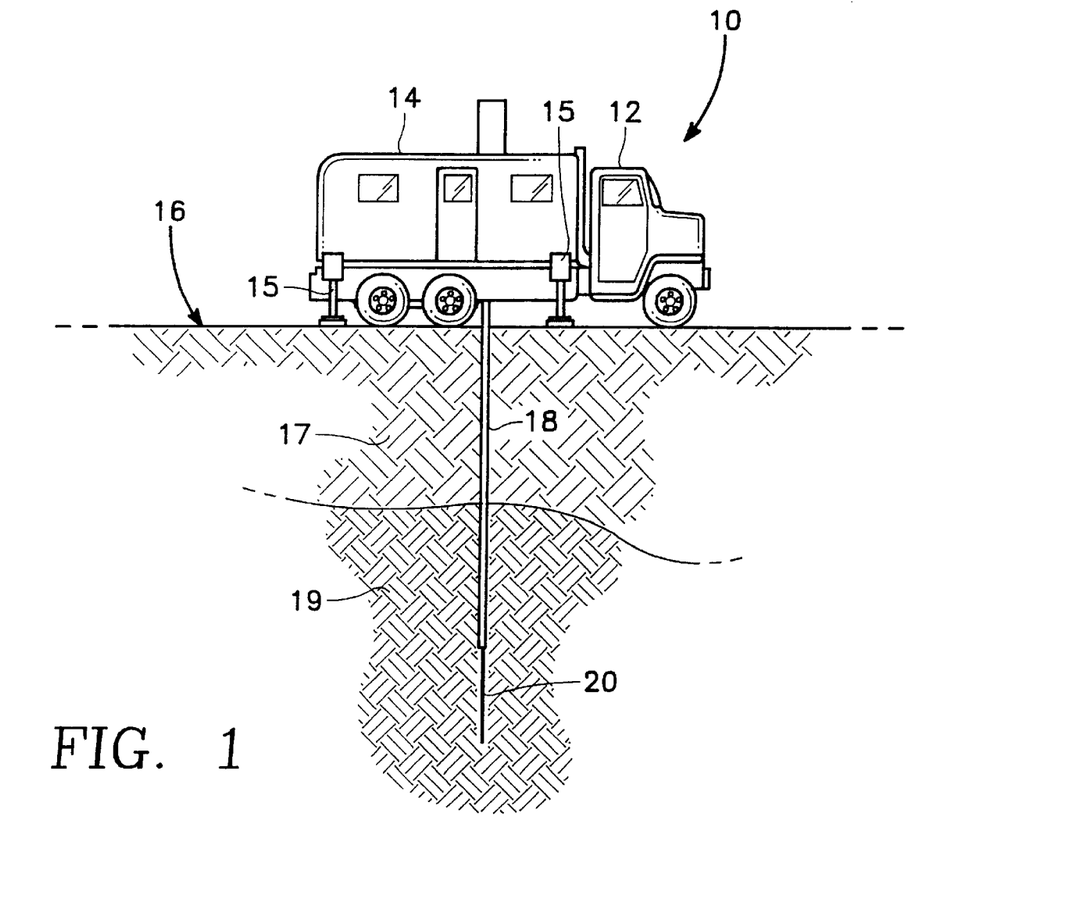
FIG. 1 is a plain view of electric cone penetration test 20 assembly used with the piezocone of the present invention.

Referring first to FIG. 1, there is shown a electric cone penetration test system 10 which may be used during environmental groundwater investigations as an efficient means of hydrogeologic site characterization and subsurface plume tracking. Test system 10 includes a 3-axle truck 12 which has mounted inside its rear compartment 14 a plurality of heaving hydraulic rams (not illustrated). Position at each corner of the rear compartment 14 of truck 12 is a leveling stanchion 15 which provides support for truck 12 and maintains truck 12 in a fixed position relative to the ground 16.

Figure 2:
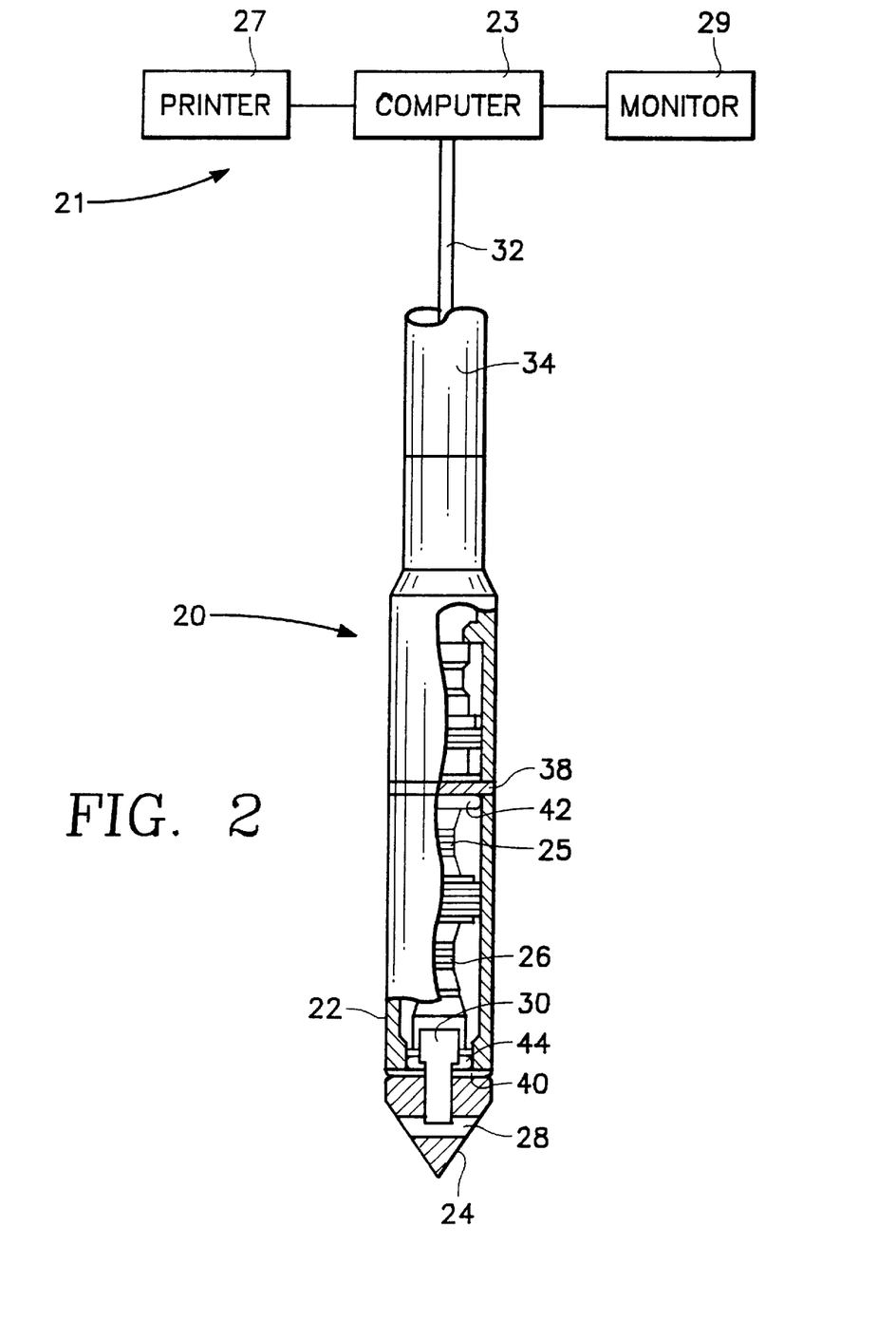
FIG. 2 is a view, in partial section, of the piezocone of the present invention.

Extending vertically downward from the underside of 3-axle truck 12 into the ground 16 is a string of steel pipes 18. Attached to the end of steel pipes 18 is a piezocone 20 which is depicted in FIG. 2 in section. Each steel pipe of the string of steel pipes 18 is approximately one meter in length and is generally pushed into the ground at a constant penetration rate of 2 cm/sec, one pipe length at a time. The pushing force exerted on pipes 18 and piezocone 20 is supplied by the hydraulic rams within compartment 14 of truck 12. The weight of truck 12 provides the reaction force to push against pipes 18 and can be as large as twenty tons.

The string of steel pipes 18 has additional pipes added to the upper end of string 18 by means of a tapered threaded joint (not illustrated).

The on board data acquisition system 21 of FIG. 2 for test system 10 converts analog electrical signals received from piezocone 20 into digital data, and then stores the data at small depth increments (typically about one inch) on a personal digital computer system 23 also mounted inside truck 12. The data is also displayed on a monitor 29 mounted inside of truck 12. A printer 27 can also be connected to the computer 23 to provide an automatic log of penetration upon completion of the test.

Referring to FIG. 2, there is shown a detailed view of piezocone 20. Piezocone 20 includes a friction sleeve 22 and a conical tip or cone 24 attached to the lower end of friction sleeve 22. Conical tip 24 is removable from friction sleeve 22. Conical tip 24 develops the end bearing component $q_c$ of penetration resistance. Friction sleeve 22 is an isolated cylindrical sleeve positioned above tip 24 which senses the resistance of the soil as sleeve 22 passes through the soil. The Friction sleeve resistance $f_s$ is determined by dividing the soil friction by the friction sleeve area. The cone resistance qc and the friction sleeve resistance $f_s$ can then be used to determine soil classification.

Mounted within friction sleeve 22 are a pair of strain gauge load cells 25 and 26 which measure the soil bearing resistance acting on conical tip 24 and the soil shear resistance sensed along the cylindrical friction sleeve 22 as piezocone 20 penetrates the ground soil 16. The pore water pressure is measured by a porous element or filter 28 mounted in conical tip 24 of piezocone 20 and a pressure transducer 30 mounted in cylindrical friction sleeve 22 of piezocone 20.

It should be noted that the porous element or filter may be mounted above the conical tip of the piezocone.

In addition, piezocone 20 also has an inclinometer (not illustrated) which is used to monitor the verticality of the environmental groundwater test performed by piezocone 20.

The test performed by piezocone 20 are recorded continuously as a function of depth and transmitted through an electrical cable 32 which extends from the upper end of piezocone 20 through a coupler 34 and pipes 18 (FIG. 1) to the rear compartment 14 of truck 12. The end of electrical cable 32 is connected to computer 23 of the on board data acquisition system 21 for test system 10 allowing test data from piezocone 20 to be transmitted to the data acquisition system 21 for test system 10.

The sleeve 22 of piezocone 20 also has at its upper end a quad ring 38 and at its lower end a quad ring 40. Similarly, there is located near the upper end of sleeve 22 an "O" ring 42, while there is located near the lower end of sleeve 22 an "O" ring 44. Quad rings 38 and 40 and "O" rings 42 and 44 function to insure that interior portion of sleeve 22 is water tight.

Figure 3:
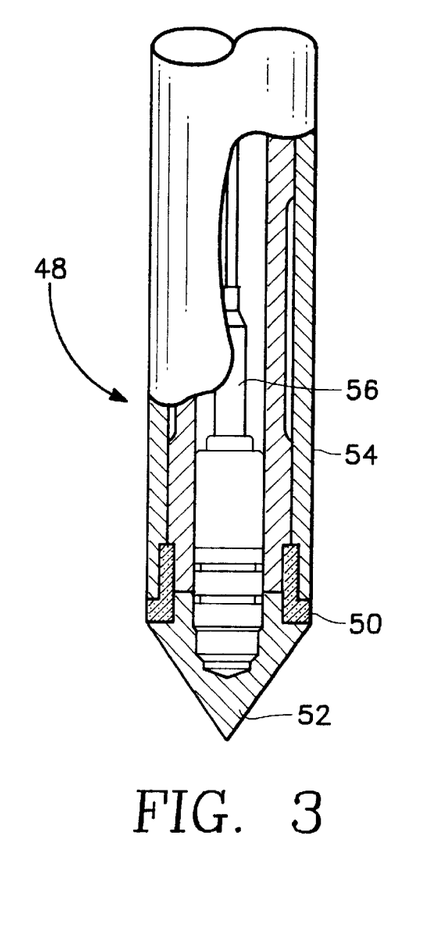
FIG. 3 is a view, in partial section, of another embodiment of the piezocone of the present invention.
Figure 4:
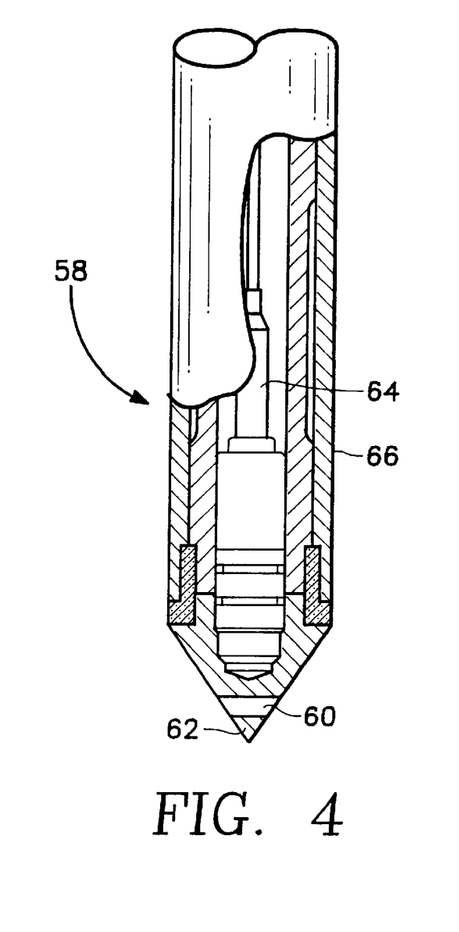
FIG. 4 is a view, in partial section, of still another embodiment of the piezocone of the present invention.

Referring to FIGS. 3 and 4, there shown alternate embodiments of the piezocone. The piezocone 48 of FIG. 3 has a porous filter 50 positioned at its outer surface between conical tip 52 and sleeve 54. The pressure transducer 56 of piezocone 48 is mounted within the interior portion of the sleeve 54 of piezocone 48.

The piezocone 58 of FIG. 4 has a porous filter 60 positioned within conical tip 62. The pressure transducer 64 of piezocone 58 is mounted within the interior portion of the sleeve 66 of piezocone 58. Porous filter 50 and porous filter 60 each have a diameter of 5 millimeters.

Figure 5:
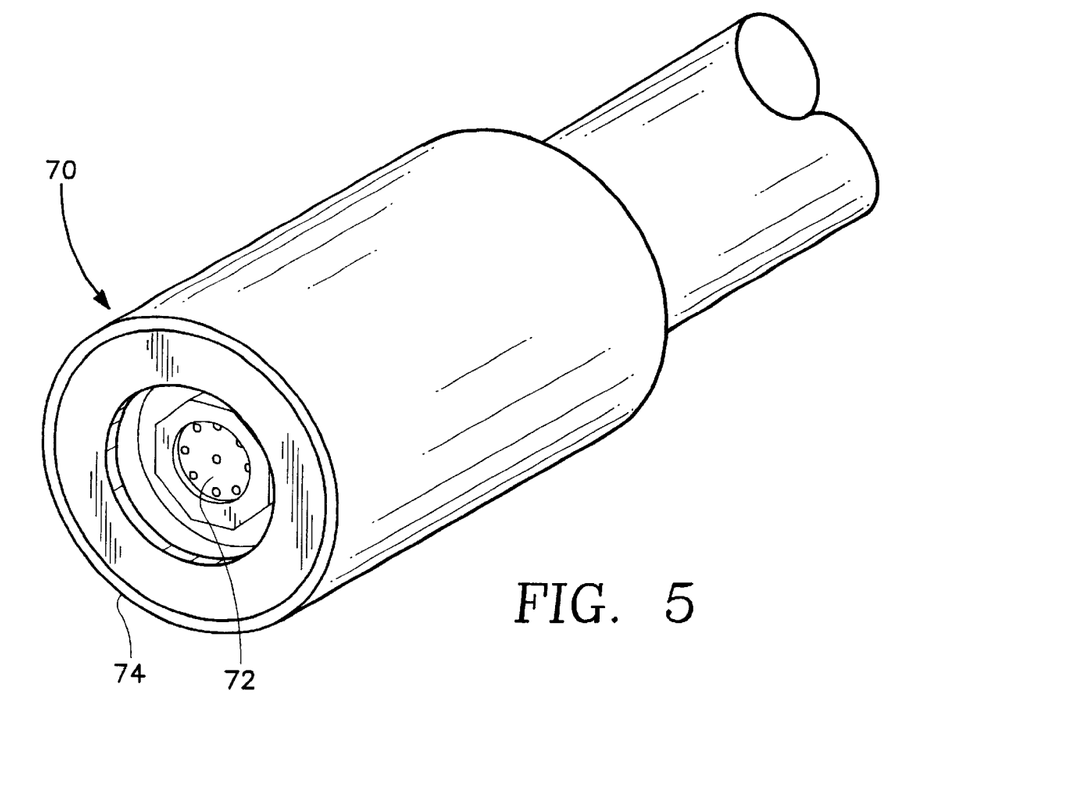
FIG. 5 is a top view of the piezocone of the present invention illustrating the placement of the pressure transducer within the sleeve of the piezocone.

Referring to FIG. 5 there is shown an end view of a piezocone 70 which has a pressure transducer 72 mounted within the sleeve 74 of piezocone 70 at the upper portion of sleeve 70.

At this time it should be noted that a piezocone commercially available from Vertek, a division of Applied Research Associates, Inc. of South Royalton, Vt. was modified to include a pressure transducer, Model No. HKM-375-25A, manufactured by Kulite Semiconductor Products, Inc. of Leonia, N.J.

Referring to FIGS. 1 and 2, the pressure transducer 30 used in the preferred embodiment of the present invention has a rated pressure of 25 psi, a maximum pressure or over pressure capacity of 500 psi, a resolution of 0.9 inches of water and a rated electrical excitation of 4 VDC. In addition, pressure transducer 30 has a combined nonlinearity, hysteresis and repeatability of plus or minus 0.1% FSO (Full Scale Output). The sensitivity of pressure transducer 30 is 1.13 mV/psi. The compensated temperature range for pressure transducer 30 is from 80 degrees fahrenheit to 180 degrees fahrenheit.

Figure 6:
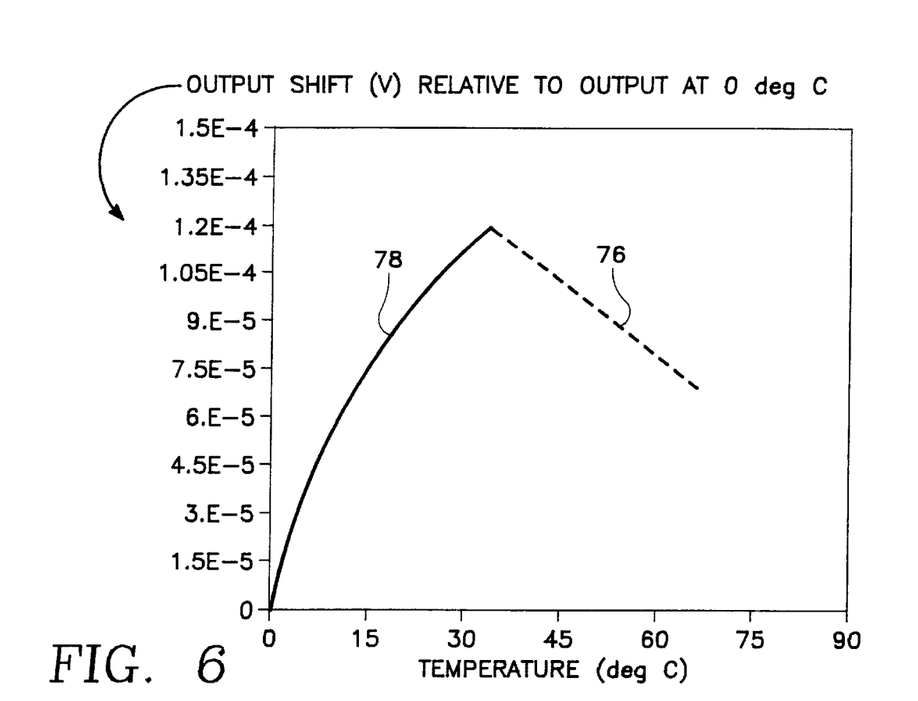
FIG. 6 is a plot illustrating the thermal sensitivity of the pressure transducer for the piezocone of FIG. 2.

The thermal sensitivity of pressure transducer 30 is illustrated in FIG. 6. Plot 76 of FIG. 6 depicts a first order curve fit of thermal sensitivity for pressure transducer 30, while plot 78 depicts a second order curve fit of thermal sensitivity for pressure transducer 30.

At this time it should be noted that each pressure transducer will have a unique thermal sensitivity plot that will vary slightly from the plot illustrated in FIG. 6.

The functional form of the output shift of pressure transducer 30 in piezocone is given by the following expressions. The output shift represents the change in output (with an excitation of 4.00V) due to temperature changes away from 0 degrees Centigrade.

$$\Delta V = 6.117 \times 10^{-6} T - 7.321 \times 10^{-8} T^2 \text{ for } 0 < T < 32° \text{ C.} \qquad (1)$$

$$\Delta V = 1.713 \times 10^{-4} - 1.578 \times 10^{-6} T \text{ for } 32 < T < 67° \text{ C.} \qquad (2)$$

$$P_i = \frac{V_{p_i} - V_{p_o} - \Delta V(T_i) + \Delta V(T_o)}{S} \qquad (3)$$

where: S=gage sensitivity=0.000566 V/psi

The conical tip 24 of piezocone 20 has a full scale range (FSR) of 33,000 lbs. a sensitivity of 7.6E-05 mV/V/lb and a nonlinearity of 0.05% calibrated range (10,000 lbs.). The sleeve 22 of piezocone 20 has a full scale range of 5,000 lbs., a sensitivity of 3.5E-04 mV/V/lb and a nonlinearity of 0.50% FSR.

The load cells 25 and 26 and pressure transducer 30 within piezocone 20 are temperature dependent. Since these elements of piezocone 20 are generally calibrated at ambient temperature, formation temperature can cause a zero shift during penetration of piezocone 20 into the ground 16 which results in errors. A temperature transducer (not illustrated is included in piezocone 20 to compensate for any zero shifts occurring during penetration of piezocone 20 into ground 16.

Referring again to FIGS. 1 and 2, during a push operation for piezocone 20, a higher pressure piezocone (250 psi) is used for the first push to identify the course grained zone/material 17 and fine grained zone/material 19 in the ground 16. During a second push, the low pressure range, high resolution piezocone 20 with approximately 25 psi full scale output is used to evaluate water levels by measuring pressures in course grained materials. Measurement of pore pressures in coarse grained materials typically takes less time than fine grain materials since equilibrium is established rapidly during dissipation in coarse grained materials.

It should be noted that the 25 psi piezocone provides better resolution than the 250 psi piezocone. It should be noted the a 250 psi range piezocone having a 250 psi pressure transducer is also commercially available from Vertek.

In addition, when a low pressure piezocone 20 advances 16, from a coarse grained material 17 to a fine grained material 19, very high excess pressure can build-up rapidly exceeding the maximum pressure capacity of piezocone 20. This is another reason for the user of test system 10 to identify fine grain zones 19 and enter the fine grain zones 19 carefully with a low pressure (25 psi) piezocone.

Vertek also provides penetration data acquisition system software (PENDAS) with the piezocone. The Vertek penetration data acquisition system software generates push data in an ASCII text format. One raw data file (*.DAT) and multiple dissipation files (*.### where ### is the approximate depth) are generated during the push. The .DAT file includes identifying information and raw data for sleeve stress, tip stress, depth and, if used, pore pressure, temperature, and seismic returns. Each dissipation file includes identifying information, sensor data, depth, and pressure values (uncorrected) per unit time (sample rate).

The user of test system 10 may generate a refined data file (*.ECP) using a PLOT subroutine within the Vertek penetration data acquisition system software. The redefined data file presents data in engineering units such as feet, psi and tsf. The redefined data file is also used as the input data file for the Piezocone Dissipation Analysis software of the microfiche appendix. The data of the file includes identifying nformation, depth, tip stress, sleeve stress and the ratio between tip and sleeve. The user may also include the following:

| | |
|---|---|
| Pore pressure | Wet Density |
| Inclination | Relative Density |
| Excitation (voltage) | Temperature |
| Overburden | Soil classification by friction ratio |
| Effective Overburden | Soil classification by pore Pressure |

When a new test is started using electric cone penetration test system 10, PENDAS prompts the user for a project name and well name. PENDAS then creates a DOS directory structure and file names for the test.

The Piezocone Dissipation Analysis (PDA) software of the microfiche appendix looks for data in the locations created by PENDAS. The Piezocone Dissipation Analysis (PDA) software of the microfiche appendix post-processes push data to calculate lithological parameters including the water depth below ground surface and the hydraulic conductivity depicted in FIG. 8. It graphically displays hydrostatic pressure vs. depth (FIG. 7), hydraulic conductivity vs. depth (FIG. 8), and dissipation data (FIG. 9). PDA automatically selects data for use in the calculations based on built-in algorithms. The user may view and select (or de-select) curves and individual data points for inclusion in the analysis. The user can also dismiss data that is obviously erroneous. The user also has the option to save settings for a particular push operation upon exiting from a file in the Piezocone Dissipation Analysis (PDA) software.

It should be noted that any data changes are temporary while the ECP file is open. These changes will not be written to the data files. The PDA program configuration changes will be written to a PDA INI file. The INI file changes can be undone by resetting the INI file to the original configuration.

The PDA software of the mocrofiche appendix looks for data in locations created by PENDAS. The PDA software of the microfiche appendix uses the ECP and dissipation files for input data. Specifically, the program uses the tip stress, temperature, and soil classification from the ECP file. All other data is obtained from the dissipation files.

Although project directories may be placed anywhere on the hard drive or on a floppy disc, the PDA software of the microfiche appendix looks first under the directory containing the PDA.EXE. When a test is selected, the PDA software jumps to the CONE subdirectory.

The user of the software of the microfiche appendix must include appropriate data when generating the ECP file. For example, if a soil classification is not generated, the PDA software of the microfiche appendix will not be able to automatically calculate hydraulic conductivity data.

To use the PDA software of the microfiche appendix the user double clicks on a PDA icon which appears on monitor 29. From an Open Entire Penetration Window, the user may select and then open a project folder such as PM24. The PDA software of the microfiche appendix scans for a CONE subdirectory and display any files with ECP extensions that it finds in the CONE subdirectory. The user may then highlight the desired ECP file and click OK. If only one ECP file is displayed, clicking OK will automatically open the ECP file. The PDA software of the microfiche appendix will read the ECP file data and any associated dissipation data from the dissipation files.

If the PDA software of the microfiche appendix looks for data that is missing, a warning message will appear on monitor 29. This is a non-fatal indicator that the PDA software analysis results may be incomplete.

A Penetrometer Dissipation Analysis window which appears on monitor 29 includes the data provided in the following Tables. The filename and a DOS path for the selected ECP file also appear on the Penetrometer Dissipation Analysis window. The ECP Filename for project folder PM24 is:

C:\DATA\016\PDA\PM24\CONE\PM24PZ1.ECP.

TABLE I

| Depth (ft) | Total Time (sec) | File WDBS (ft) | Final Pres (psi) | Hyd Static (psi) | Diss Complete | Show Diss Curve | Dismiss Hyd Cond |
|---|---|---|---|---|---|---|---|
| 5.42 | 138 | −10.23 | −2.08 | −1.50 | | | x |
| 8.01 | 618 | −32.55 | 17.58 | −0.37 | | | x |
| 10.09 | 420 | −25.06 | 15.23 | 0.53 | | | x |
| 11.88 | 150 | −27.77 | 17.18 | 1.30 | | | x |
| 14.00 | 66 | 8.15 | 2.54 | 2.20 | x | | |
| 16.02 | 84 | 8.73 | 3.16 | 3.10 | x | | |
| 19.91 | 66 | 9.47 | 4.52 | 4.80 | x | | |
| 23.88 | 60 | 10.67 | 5.73 | 6.50 | | | x |
| 27.91 | 234 | 9.14 | 8.13 | 8.30 | x | | |
| 31.92 | 210 | 8.94 | 9.96 | 10.00 | x | | |

TABLE II

| Depth (ft) | Hyd Cond (cm/s) | $T_{50}$ (sec) | Tip Res (tsf) | Soil Type | Errors |
|---|---|---|---|---|---|
| 5.42 | 3.07E − 7 | 131.1 | 184.8 | Sand | * |
| 8.01 | 3.35E − 6 | 84.4 | 9.0 | ML | * |
| 10.09 | 9.65E − 5 | 24.0 | 6.7 | OH | * |
| 11.88 | 2.10E − 5 | 22.3 | 4.4 | CL | * |
| 14.00 | 6.85E − 6 | 6.2 | 123.2 | Sand | |
| 16.02 | 8.93E − 6 | 7.9 | 100.6 | Sand | |
| 19.91 | 8.00E − 6 | 10.1 | 124.2 | Sand | |
| 23.88 | 5.30E − 6 | 5.8 | 247.7 | Sand | * |
| 27.91 | 6.93E − 7 | 50.9 | 202.8 | Sand | |
| 31.92 | 1.05E − 6 | 40.5 | 175.6 | Sand | |

WDBS Estimate: 8.87 Penetrometer Diameter: 1.406"
Pearson's rΛ2: 0.999 Cone ID: 0128.045.0
Water Table: 91.13
Surface Elevation: 100.00

The tabular data which appears on the Penetrometer Dissipation Analysis Window and is provided by Tables I and II consist of the following information.

1. Depth which list the depth of piezocone 20 (pore pressure element for each dissipation test.
2. Total Time is the overall dissipation test time.
3. WDBS (Water Depth Below Surface) slope is variable and based on a best fit line of all the complete dissipations of a push operations unless: (1) the user chooses a fixed Lslope (density of fresh water); or (2) there is only one complete dissipation (density of fresh water). File WDBS is based on either (1) the WDBS slope if one or more dissipations are complete; or (2) the density of fresh water if no dissipation is complete.
4. Final Pressure is the last or lowest pressure measured during the dissipation test.

5. Hydrostatic Pressure is a point along the WDBS curve which is calculated based upon probe depth.
6. Diss Complete is a checkbox that, when checked, indicates whether the dissipation is complete. The Piezocone Dissipation Analysis program initially determines which points represent complete dissipations. The points can also be manually selected and de-selected to override automatic choices made by the program.
7. Show Diss Curve is a checkbox that shows or hides the dissipation curves, one of which is illustrated in FIG. 9.
8. Dismiss Hyd Cond is a checkbox that shows or hides the hydraulic conductivity values in the Hydraulic Conductivity Profile window illustrated in FIG. 8. Points will be included automatically if sufficient data exists to calculate the points and there are no errors in the calculation. The points can also be manually selected and de-selected to override the automatic choices.
9. Hyd Cond (cm/s) is the calculated hydraulic conductivity value. A blank indicates that there insufficient data to calculate the hydraulic conductivity value. It should be noted that a soil type must be available to calculate hydraulic conductivity.
10. $T_{50}$ is the time required for 50% of the excess pressure to dissipate.
11. Tip Res is the tip resistance interpolated for depth from the ECP file. The user may click on this box and enter a new value in the change window to manually change tip resistance. The new data value for tip resistance will be retained in memory only while the ECP file is open. This value is not written to the ECP file.
12. Soil Type is the soil classification taken from the ECP file, if the soil classification is available. The user may click on this box and select a new soil type from a drop-down list of soil types to manually change the soil type. The new data value for the soil type will be retained in memory only while the ECP file is open. This value is not written to the ECP file. Soil type is based on Friction Ratio or Pore Pressure.
13. Errors are indicated if the final pressure or the File WDBS is negative, the depth is less than overall WDBS (if at least one dissipation is complete), or an error occurs when calculating a new $T_{50}$ based on the hydrostatic pressure. Additional data which appears on the Penetrometer Dissipation Analysis Window and is provided below Tables I and II consist of the following information.

1. WDBS Estimate is based on the Hydrostatic Pressure Profile curve zero pressure intercept. If the fixed slope option is selected, the slope is fixed at 0.433 psi/ft (pure water) and fit to the complete dissipation points. If the variable slope option is selected it will be fit to the complete dissipation points using a linear regression 20 technique
2. Pearson's rΛ2 is a measure of data correlation where 1.000 is an optimum value.
3. Water Table is calculated by subtracting the WDBS Estimate from the surface elevation. The Water Table is blank if a surface elevation is not entered by the user.
4. Surface Elevation—The user may click on the box to enter the surface elevation.
5. Penetrometer Diameter—The user may click on the box to enter the current penetrometer diameter.
6. Cone ID is reprinted from the ECP file.

The Penetrometer Dissipation Analysis Window includes a File pull down menu. The File pull down menu includes: (1) Open Penetration which opens the Open Entire Penetration window and allows the user to select a new ECP file and its associated data for processing; (2) Open Processed Push File which opens the current ECP file in a text editor that is configured under Windows; (3) Output Conductivity Profile which opens a window that allows the user to save hydraulic conductivity data in tabular form, plain text format.

There is also a Print profile which includes the following: (1) Hydraulic Conductivity Figure which prints the hydraulic conductivity window and requires at least one error-free hydraulic conductivity point; (2) Dissipation Figure which prints the currently selected dissipation curve window; and (3) Hydrostatic Pressure Slope which prints the hydrostatic pressure profile window.

The Penetrometer Dissipation Analysis Window also includes an Options pull down menu. The Options pull down menu has a (1) Reset INI File which restores program defaults for window position, dissipation threshold, and hydrostatic pressure slope; and (2) Complete Dissipation threshold (feet) which specifies the allowable data variation around the hydrostatic pressure slope. The PDA program of the microfiche appendix considers the data points within this range to be complete dissipations.

Figure 7:
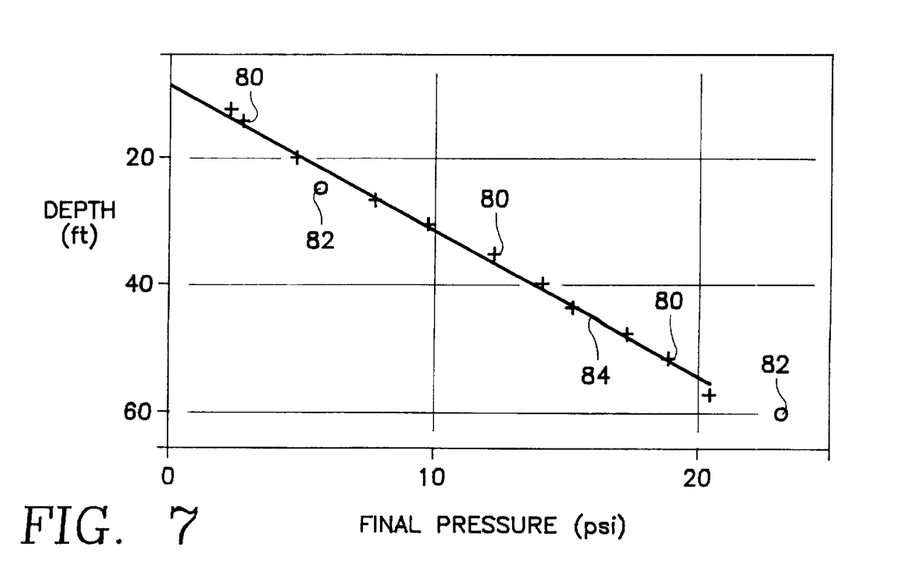
FIG. 7 is a plot illustrating a Hydrostatic Pressure Profile for a first cone penetration test which is generated by the Program of the microfiche appendix.

The Options pull down menu also has a Hydrostatic Pressure Slope which allows the user to select a fixed slope option (0.433 psi/ft which equates to pure water at STP) or a variable slope option (best-fit linear regression) for the Hydrostatic Pressure Profile of FIG. 7.

The Window pull down menu of the Penetrometer Dissipation Analysis Window includes (1) Water Depth which restores and selects the Hydrostatic Pressure Profile window if it has been closed, minimized or hidden; and (2) Hydraulic Conductivity which restores and selects the Hydraulic Conductivity window if it has been closed, minimized, or hidden.

The Help pull down menu of the Penetrometer Dissipation Analysis Window provides selected program information.

Figure 8:
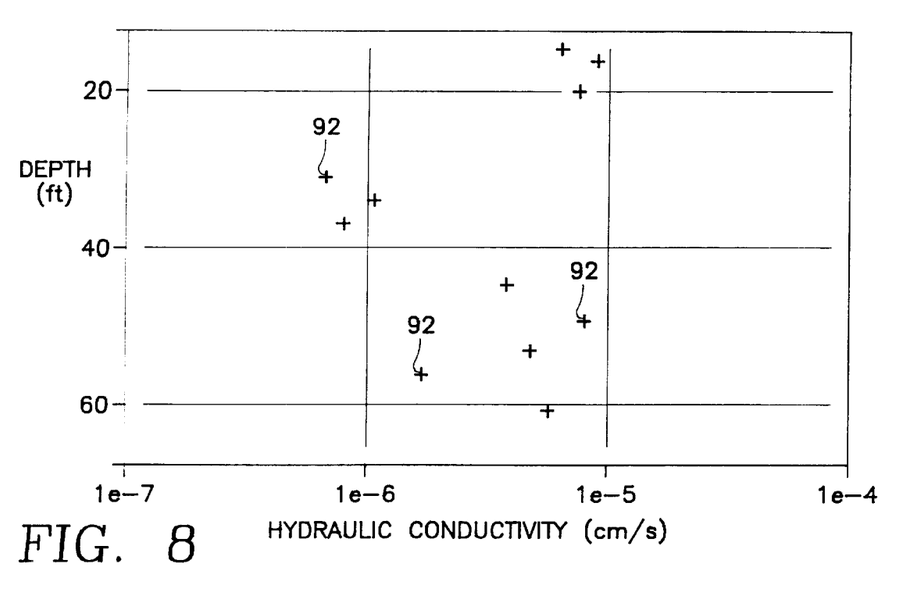
FIG. 8 is a plot illustrating a Hydraulic Conductivity Profile for the cone penetration test depicted in FIG. 7.
Figure 9:
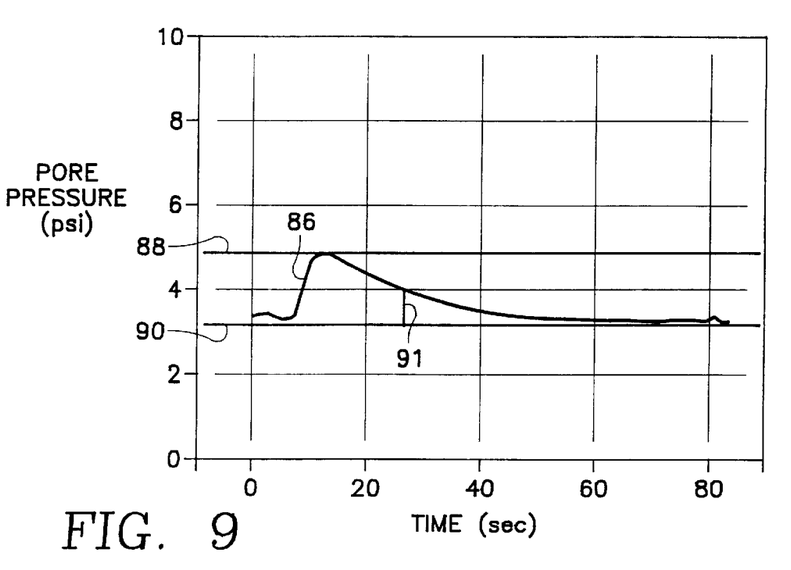
FIG. 9 is a plot illustrating a pressure dissipation curve for a selected depth of the cone penetration test depicted in FIG. 7.

Referring to FIGS. 7, 8 and 9, FIG. 7 depicts a Hydrostatic Pressure Profile curve which illustrates the final pressure points 80 for completed dissipation data sets and the final pressure points 82 for incomplete dissipation data sets. A best fit line 84 is drawn through the final pressure points 80 for the completed dissipation data sets. Line 84 can have a fixed slope or a variable slope which fits the final pressure points 80 for the completed dissipation data sets. Line 84 intersects the Y axis at the estimated water depth below surface.

FIG. 9 illustrates a pressure dissipation plot for a selected depth of 16.02 feet along with the same data that is provided in Tables I and II. The final pressure for the pressure dissipation curve 86 is 3.16 psi.

There is a dissipation file created for each depth shown in Tables I and II above. Thus, there is dissipation created for the depth of 14.00 feet, the depth of 16.02 feet and the depth of 19.91 feet. The PDA software of the microfiche appendix generates a pressure versus time plot for each dissipation file it opens.

The PDA software of the microfiche appendix first determines a final pressure for each depth. For example, the final pressure at the depth of 16.02 feet is 3.16 psi which is the equilibrium pressure at a depth of 16.02 feet.

The pressure versus time curve 86 for each dissipation file is also plotted by the software of the microfiche appendix. The PDA software of the microfiche appendix plots each pressure versus time curve 86 for the depths listed in the Penetrometer Dissipation Analysis window. The PDA software next eliminates the depths which do not meet the allowable data variation around the hydrostatic pressure slope. For example, the PDA software of the microfiche appendix eliminates the Final Pressure of 5.73 psi for the depth of 23.88 feet since the final pressure at this depth does meet the allowable data variation around the hydrostatic pressure slope. These non-allowable Final Pressures are represented by the reference numeral 82 in FIG. 7. The software of the microfiche appendix then plots best fit line 84. The Water Depth Below Surface Estimate for the best fit line 84 is 8.87 feet which is the zero pressure intercept for the hydrostatic pressure line 84.

The software of the microfiche appendix determines the overall hydrostatic pressure using the Water Depth Below Surface Estimate of 8.87 feet and the depth of the probe or piezocone which is 16.02 feet for FIG. 7. This results in a difference of 0.06 psi between the Final Pressure of 3.16 psi and the Hydrostatic Pressure of 3.10 psi for a depth of 16.02 feet.

Whenever the Final Pressure is substantially different from the Hydrostatic Pressure, the software of the microfiche appendix ignores the Final Pressure when it plots the best fit line 84 of FIG. 7. For example the software of the microfiche appendix ignores the final pressure of 5.73 psi at a depth of 23.88 feet since the difference between the final pressure and the hydrostatic pressure is 0.77 psi (6.50 psi–5.73 psi=0.77 psi). The Diss Complete in Table I identifies with an "X" the final pressures which are used to plot the best fit line 84 of FIG. 7.

Referring to FIG. 9, the PDA software of the microfiche appendix then determines the pressure and the time when the pressure starts to decay which occurs at boundary 88 as well as the pressure and the time when the pressure reaches its asymptote which is boundary 90.

The PDA software of the microfiche appendix next determines the time $T_{50}$. The user may edit tip resistance, soil type and the positions of the boundary lines 88 and 90 of FIG. 9. The boundary lines 88 and 90 may be moved or down by placing the screen cursor on the line 88 or 90 and dragging the line 88 or 90 to its new position. When the dissipation plot opens the boundaries 88 and 90 are automatically set at the maximum and minimum pressures.

$T_{50}$ is derived by determining the time at which the pressure dissipates 50% which occurs at line 91. $T_{50}$ is equal to the time at which the pressure dissipates 50% minus the time at which the pressure is at its peak. For the plot of FIG. 9, $T_{50}$ is approximately 7.9 seconds. For the plot of FIG. 9, the time at which 50% pressure dissipation occurs is about 22.9 seconds and the time at which the pressure is at its peak is about 15 seconds.

FIG. 8 provides a visual indication of the calculated hydraulic conductivity (indicated generally by points 92) for all depths that have not been dismissed.

In operation, when the user selects a push folder, the PDA program of the microfiche appendix calculates a WDBS (water depth below surface) for each dissipation curve, fits a straight line to the dissipation data points for all the dissipation curves and then determines an overall WDBS. The straight line has a slope equal to the nominal density of water which 62.4 pcf or 0.433 psi if the user selects the fixed slope option. If the user selects the variable slope option the slope of the line is based on a best fit curve. The PDA program assumes that for any individual WDBS that deviates from the overall WDBS by more than ±0.5 feet, the pressure dissipation curve is incomplete and the individual WDBS is deleted from the calculation. The Options pull down menu allows the user to select the tolerance so that it does not have to be ±0.5 feet.

A final WDBS is determined based on fitting another straight line (slope=density of water) to the remaining individual WDBS data. This data and the curve are displayed in the Hydrostatic Pressure Profile window illustrated by FIG. 7. The calculated WDBS assumes that hydraulic pressure is attributable to water only at Standard Temperature and Pressure which is 68° F. and 14.7 psi.

The software output data for each push may be saved in a text file. An example of this file is as follows:
Test ID: PIEZO 01
Site: ir site 24
Date: 10/09/96
Time: 17:16:35
Water Table: 12.45

| Depth | Cond | Soil |
|---|---|---|
| 14.00 | 1.8E-6 | CL |
| 16.02 | 2.4E-6 | CL |
| 19.91 | 2.2E-6 | CL |
| 27.91 | 1.9E-7 | CL |
| 31.92 | 2.9E-7 | CL |
| 35.95 | 2.1E-7 | CL |
| 40.03 | 2.9E-6 | CL |
| 44.41 | 1.1E-6 | CL |
| 48.46 | 2.2E-6 | CL |
| 52.50 | 1.3E-6 | CL |
| 56.44 | 4.5E-7 | CL |
| 60.49 | 1.6E-6 | CL | where Cond is hydraulic conductivity in cm/second and Soil is the soil type.

Figure 10:
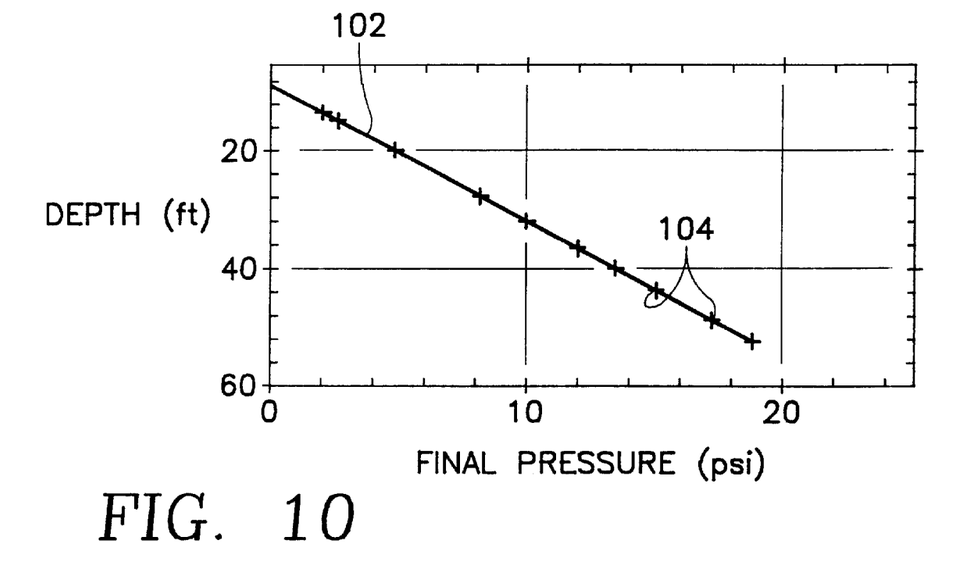
FIG. 10 is a plot illustrating a Hydrostatic Pressure Profile for a second cone penetration test which is generated by the Program of the microfiche appendix.
Figure 11:
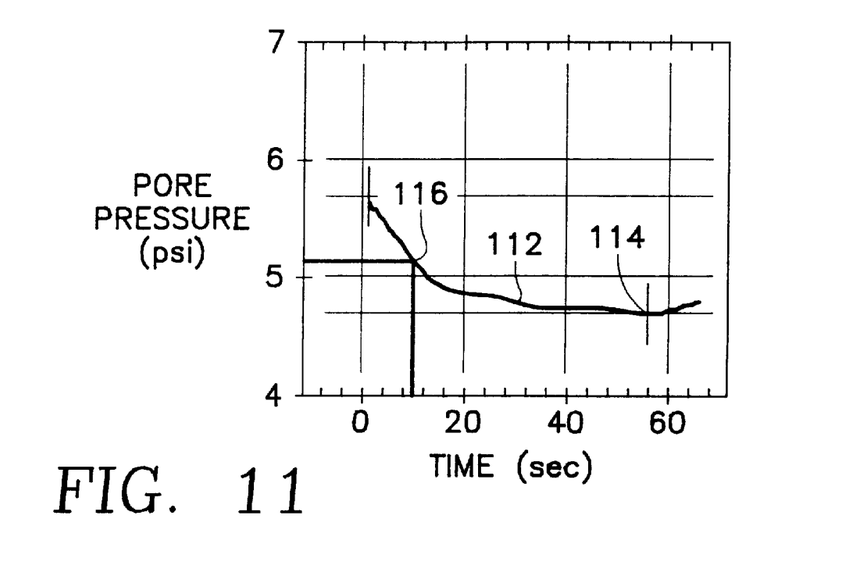
FIG. 11 is a plot illustrating a pressure dissipation curve for a selected depth of the cone penetration test depicted in FIG. 10.
Figure 12:
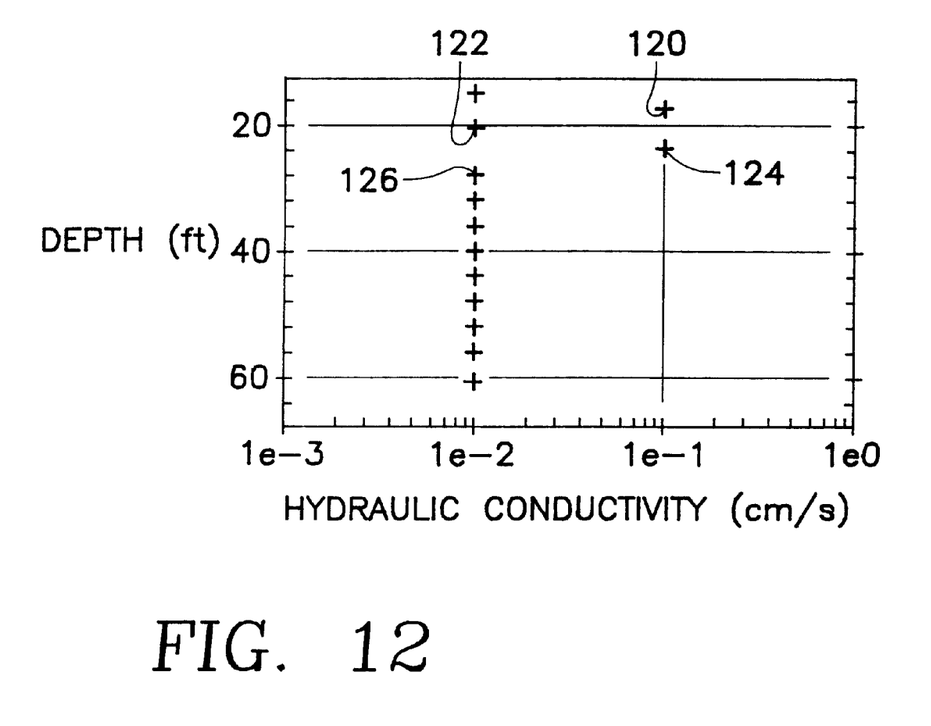
FIG. 12 is a plot illustrating a Hydraulic Conductivity Profile for the cone penetration test depicted in FIG. 10.

Referring to FIGS. 1, 10, 11 and 12, the PDA software of the microfiche appendix also uses Robertson CPT Soil Classification lookup table to generate the Hydraulic Conductivity profile depicted in FIG. 12. The Robertson CPT Soil Classification lookup table is set forth as follows.

TABLE III

| Description | Coefficient of Permeability (cm/s) |
|---|---|
| Sensitive, Fine Grained | $10^{-5}$ |
| Organic Soils-Peats | $10^{-5}$ |
| Clays-Clay to Silty Clay | $10^{-7}$ |
| Silt Mixtures-Clayey Silt to Silty Clay | $10^{-6}$ |
| Sand Mixtures-Silty Sand to Sandy Silt | $10^{-4}$ |
| Sands-Clean Sand to Silty Sand | $10^{-2}$ |
| Gravelly Sand to Sand | $10^{-1}$ |
| Very Stiff Sand to Clayey Sand | $10^{-5}$ |
| Very Stiff, Fine Grained | $10^{-6}$ |

The software of the microfiche appendix provides for an option which allows the user of test system 10 to include the Coefficient of Permeability of the Robertson CPT Soil Classification lookup table in the Penetrometer Dissipation Analysis window which appears on monitor 29 as is best illustrated in the following tables.

TABLE IV

| Depth (ft) | Total Time (sec) | File WDBS (ft) | Final Pres (psi) | Hyd Static (psi) | Diss Complete | Show Diss Curve | Dismiss Hyd Cond |
|---|---|---|---|---|---|---|---|
| 5.42 | 138 | 10.23 | -2.08 | -1.45 | | | x |
| 8.01 | 618 | -32.55 | 17.58 | -0.37 | | | x |
| 10.09 | 420 | -25.06 | 15.23 | 0.58 | | | x |
| 11.88 | 150 | -27.77 | 17.18 | 1.35 | | | x |
| 14.00 | 66 | 8.15 | 2.54 | 2.27 | x | | |
| 16.02 | 84 | 8.73 | 3.16 | 3.14 | x | | |
| 19.91 | 66 | 9.47 | 4.52 | 4.83 | x | | |
| 23.88 | 60 | 10.67 | 5.73 | 6.55 | | | x |

TABLE IV-continued

| Depth (ft) | Total Time (sec) | File WDBS (ft) | Final Pres (psi) | Hyd Static (psi) | Diss Complete | Show Diss Curve | Dismiss Hyd Cond |
|---|---|---|---|---|---|---|---|
| 27.91 | 234 | 9.14 | 8.13 | 8.29 | x | | |
| 31.92 | 210 | 8.94 | 9.96 | 10.00 | x | | |

TABLE V

| Depth (ft) | Hyd Cond (cm/s) | $T_{50}$ (sec) | Tip Res (tsf) | Soil Type | Errors |
|---|---|---|---|---|---|
| 5.42 | 1.00E - 1 | 13.5 | 184.8 | Sand | * |
| 8.01 | 1.00E - 4 | 84.4 | 9.0 | ML | * |
| 10.09 | 1.00E - 6 | 24.0 | 6.7 | OH | * |
| 11.88 | 1.00E - 7 | 22.3 | 4.4 | CL | * |
| 14.00 | 1.00E - 2 | 6.2 | 123.2 | Sand | |
| 16.02 | 1.00E - 1 | 7.9 | 100.6 | Sand | |
| 19.91 | 1.00E - 2 | 10.0 | 124.2 | Sand | |
| 23.88 | 1.00E - 1 | 5.8 | 247.7 | Sand | |
| 27.91 | 1.00E - 2 | 50.9 | 202.8 | Sand | |
| 31.92 | 1.00E - 2 | 40.5 | 175.6 | Sand | |

WDBS Estimate: 8.77 Penetrometer Diameter: 1.406"
Pearson's r^2: 0.999 Cone ID: 0128.045.0
Water Table:
Surface Elevation:

Referring to Tables IV and V, when the depth of penetration of probe 20 (FIG. 1) is 11.88 feet, the soil type is clay. The Coefficient of Permeability provided by the Robertson CPT Soil Classification lookup table for clay is $10^{-7}$ cm/s. For a depth of 11.88 feet the Penetrometer Dissipation Analysis window recites a hydraulic conductivity (i.e. Coefficient of Permeability) of 1.00E-7 cm/s as shown in Table V.

Similarly, when the depth of penetration of probe 20 is 8.01 feet, the soil type is a sand mixture-silty sand to sandy silt. The Coefficient of Permeability provided by the Robertson CPT Soil Classification standard for a sand mixture is $10^{-4}$. For a depth of 8.01 feet the Penetrometer Dissipation Analysis window recites a hydraulic conductivity (i.e. Coefficient of Permeability) of 1.00E-4 cm/s as shown in Table V.

A third example from Table V depicts a soil type OH (silt mixtures) for a depth of penetration of probe 20 of 10.09 feet. The Coefficient of Permeability provided by the Robertson CPT Soil Classification standard for a silt mixture is $10^{-6}$ cm/s. Table V recites a hydraulic conductivity (i.e. Coefficient of Permeability) of 1.00E-6 cm/s for a depth of 10.09 feet.

FIG. 12 is a plot illustrating the hydraulic conductivity as a function of depth for one push operation of probe 20 into ground 16 which includes the hydraulic conductivity data of Table V. For example, at a depth 16.02 feet the hydraulic conductivity is 1.00E-1 cm/s which is depicted in FIG. 12 by the reference numeral 120. Similarly, at a depth of 19.91 feet the hydraulic conductivity is 1.00E-2 cm/s which is depicted in FIG. 12 by the reference numeral 122. For a depth of 23.88 feet the hydraulic conductivity is 1.00E-1 cm/s which is depicted in FIG. 12 by the reference numeral 124. Further, for a depth of 27.91 feet the hydraulic conductivity is 1.00E-2 cm/s which is depicted in FIG. 12 by the reference numeral 126.

FIG. 10 is a plot of the final pressure as a function of depth for each depth of penetration by probe 20 during the push operation illustrated in Tables IV and V. A best fit line 102 is drawn through the final pressure points 104 for the completed dissipation data sets. Line 102 intersects the Y axis at the estimated water depth below surface which is 8.77 feet.

FIG. 11 illustrates the pressure dissipation curve 112 for a depth of 19.91 feet. The final pressure for curve 112, which is depicted by the reference numeral 114, is 4.53 psi. $T_{50}$ for curve 112 is 10.0 seconds and is depicted by the reference numeral 116.

The equation used by the PDA program of the microfiche appendix to calculate Hydraulic Conductivity is as follows.

$$k = \frac{r^2}{279.12 \times t_{50} \times \alpha \times q_c} \quad (4)$$

where:
k=hydraulic conductivity (cm/sec)
r=probe radius (cm)
$T_{50}$ =time required for 50% pressure dissipation (sec)
α=empirical average coefficient for soil type
$q_c$=tip resistance (tsf)

The PENDAS software includes a file for the tip resistance of probe 20. The empirical average coefficient for soil type is found using the Sanglerat soil type index.

It should be noted that there are equations which may be used to calculate hydraulic conductivity in addition to the equation set forth above.

CThe equation used by the PDA program of the microfiche appendix to calculate Water Depth Below Surface is as follows.

$$WDBS = MD - \frac{p_p \times 144}{d_w} \quad (5)$$

where:
MD=measured depth (ft)
WDBS=water depth below surface (ft)
$p_p$=equilibrium hydraulic pressure (psi)
$d_w$=density of fresh water (lbs/cf) at STP which is 62.4 lbs/cf There is a two dimensional lookup table for different soil types versus tip resistance which provides a range of Alphas as shown below for various soil types including low plasticity clay, low plasticity silts, highly plastic silts & clay, organic loam and sand.

| | | |
|---|---|---|
| $q_c$ < 7 bar | 3 < α < 8 | Low plasticity clay (CL) |
| 7 < $q_c$ < 20 bar | 2 < α < 5 | Low plasticity clay (CL) |
| $q_c$ > 20 bar | 1 < α < 2.5 | Low plasticity clay (CL) |
| $q_c$ > 20 bar | 3 < α < 6 | Low plasticity silts (ML) |
| $q_c$ < 20 bar | 1 < α < 3 | Low plasticity silts (ML) |
| $q_c$ < 20 bar | 2 < α < 6 | Highly plastic silts & clay |
| $q_c$ < 12 bar | 2 < α < 8 | Organic loam (OL) |
| $q_c$ < 50 bar | α = 2 | Sand |
| 50 < $q_c$ < 100 bar | α = 1.75 | Sand |
| $q_c$ > 100 bar | α = 1.5 | Sand |

It should be noted one bar is equal to approximately 2089 psf. It should also be noted that the value selected for alpha is the midpoint within each range of Alphas. If, for example, qc is less than 7 bar and the soil type is low plasticity clay than the selected value for alpha is 5.5.

The software of the microfiche appendix. A includes a main program which is identified as "PDAmain". PDAmain allows the user to open the files in the software of the microfiche appendix. PDAmain also controls the reading of the files, closing of the program when the program is completed and the menu options.

Traces is the software unit in the microfiche appendix which contains the data for each dissipation plot which is generated from pore pressure measurements made during a push operation by system 10. Each dissipation plot or curve has a trace object associated with the plot. The trace object for each dissipation plot includes a start time, starting pressure, ending time, ending pressure and $T_{50}$. It should be noted that there is a trace object for each depth of a push operation by system 10. FIG. 9 illustrates a dissipation plot or curve 86 for Tables I and II, while FIG. 11 illustrates a dissipation plot or curve for Table IV and V. Traces is an embedded object code.

Figunit is the software unit/program in the microfiche appendix for controlling the figure window (FIG. 9) which depicts the Dissipation curves. Figunit creates a FigWin object which includes the trace object for each dissipation plot.

Wdbsunit is the source code for the Hydrostatic Pressure Profile plot and data illustrated in FIGS. 7 and 10. Wdbsunit uses the final pressure from each dissipation curve generated during a push operation and then plots the final pressure for each dissipation curve to generate a Hydrostatic Pressure Profile plot and a water depth below surface for the push operation. The Hydrostatic Pressure profile of FIG. 7 has a water depth below surface estimate of 8.87 feet, while the Hydrostatic Pressure profile of FIG. 11 has a water depth below surface estimate of 8.77 feet. Wdbsunit also provides a water depth below surface for each depth of a push operation of electric cone penetration test system 10

PermUnit is the source code for the Hydraulic Conductivity Profile or plot illustrated in FIG. 8 and FIG. 12. PermUnit draws the Hydraulic Conductivity Profile using the Hydraulic Conductivity for each depth of a push operation.

Optionu (Option unit) is the source code which allows the user to select options such as the Hydrostatic Pressure Slope of FIG. 7 which the user may select as a fixed slope or a variable slope. Optionu also includes the Robertson CPT Soil Classification lookup table for the various soil types which may be encountered during a push operation by Tempunit is the source code which is used for temperature compensation of the high resolution cone which is piezocone 20. Temperature calibration curves for piezocone 20 are provided by the manufacturer of piezocone 20 and the data contained therein is entered through a dialogue box into an external TempCal file which is ASCII file. The PDA program reads the data from the TempCal file and the Cone ID to determine whether there is calibration data for the piezocone. The calibration data allows for temperature compensation of the final pressure.

About opens an About Box which appears on monitor 29. Similarly, Elevunit opens a box which allows the user of system to enter a surface elevation in the Penetrometer Dissipation Analysis window. SoilUnit allows the user to designate the soil type at a particular depth.

The PDA software opens all dissipation files for a push operation, generates a FigWin for each dissipation file and then determine the starting pressure and final pressure for each dissipation file. $T_{50}$ is also calculated for each dissipation file of a push operation. The PDA software determines whether the dissipation is complete for each depth of a push operation. The PDA software also opens the file WDBS for each depth of a push operation by electric cone penetration test system 10.

From the foregoing, it may readily be seen that the present invention comprises a new, unique and exceedingly useful cone tipped cylindrical probe for use in ground water testing which constitutes a considerable improvement over the known prior art. Many modifications and variations of the present invention are possible in light of the above teachings. It is to be understood that within the scope of the appended claims the invention may be practiced otherwise than as specifically described.

What is claimed is:

1. An in soil testing system for measuring soil parameters while being forcibly penetrated into the soil comprising:
   a probe having a plurality of sensors for measuring said soil parameters;
   said plurality of sensors including:
   first and second strain gauge load cells mounted within said probe, said first strain gauge load cell measuring forces resisting tip penetration by said probe, said second strain gauge load cell measuring lateral forces resisting penetration by said probe; and
   a pressure sensing device for measuring said pore water pressure in the soil at said plurality of depths of penetration, said pressure sensing device including a porous filter mounted in a conical tip of said probe and a pressure transducer mounted within said probe, said pressure transducer being connected to said porous filter;
   said plurality of sensors of said probe generating electrical signals representative of said soil parameters;
   means coupled to said probe for forcibly penetrating said probe into the soil;
   a digital computer coupled to said plurality of sensors to receive said electrical signals from said plurality of sensors, said digital computers processing said electrical signals to provide a designation of a soil type for the soil, a pressure dissipation curve for said pore water pressure in the soil at each of said plurality of depths of penetration of said probe and a time $T_{50}$ required for a fifty percent pressure dissipation of said pressure dissipation curve at each of said plurality of depths of penetration of said probe;
   said digital computer calculating a hydraulic conductivity for each of said plurality of depths of penetration of said probe using the formula:

$$k = \frac{r^2}{279.12 \times t_{50} \times \alpha \times q_c}$$

where r is a radius for said probe stored in said digital computer, a is an empirical average coefficient for said soil type, and $q_c$ is an end bearing component of the forces resisting tip penetration by said probe;
   said digital computer calculating a water depth below surface for each of said plurality of depths of penetration of said probe using the formula:

$$WDBS = MD - \frac{p_p \times 144}{d_w} \quad (5)$$

where MD is a measured depth for said probe, $p_p$ is a final pressure for said pressure dissipation curve and $d_w$ is a density for fresh water which is approximately 62.4 pounds per cubic foot;
   said digital computer generating a hydrostatic pressure profile which illustrates a final pressure point for the pressure dissipation curve of each of said plurality of depths of penetration of said probe;
   said digital computer providing a best fit line for the final pressure point of only completed pressure dissipation curves for each of said plurality of depths of penetration of said probe;
   a monitor coupled to said digital computer for displaying a penetrometer dissipation analysis window which includes the hydraulic conductivity and the water depth below surface calculated by said digital computer for each of said plurality of depths of penetration of said probe, said monitor displaying said hydrostatic pressure profile and said best fit line;
   said digital computer containing a Piezocone Dissipation Analysis computer software program, said Piezocone Dissipation Analysis computer software program calculating said hydraulic conductivity and said water depth below surface for each of said plurality of depths of penetration of said probe, said Piezocone Dissipation Analysis computer software program generating said hydrostatic pressure profile and said best fit line;
   said Piezocone Dissipation Analysis computer software program including an option program module, said option program module having an option which allows a user of said in soil testing system to select said option, said option when selected by said user providing a Coefficient of Permeability from a soil classification lookup table for each of said plurality of depths of penetration of said probe;
   said Piezocone Dissipation Analysis computer software program using said Coefficient of Permeability from said soil classification lookup table for each of said plurality of depths of penetration of said probe to generate a hydraulic conductivity profile, said hydraulic conductivity profile appearing on said monitor.

2. The in soil testing system of claim 1 wherein said means for forcibly penetrating said probe into the soil comprises:
   a three axil truck having a plurality of hydraulic rams mounted inside a rear compartment of said three axil truck; and
   a string of steel pipes having one end extending vertically downward from an underside of said three axile truck into the soil, said probe being attached to the opposite end of said string of steel pipes, said string of steel pipes being pushed into the soil at a constant penetration rate of two centimeters per second.

3. The in soil testing system of claim 1 wherein said string of steel pipes comprises a plurality of steel pipes, each of said plurality of steel pipes having a length of approximately one meter.

4. The in soil testing system of claim 1 wherein said soil classification lookup table comprises a Robertson cone penetration test soil classification lookup table having coefficients of permeability for a variety of soil types, said coefficients of permeability for said variety of soil types ranging from $10^{-1}$ cm/sec to $10^{-7}$ cm/sec.

5. The in soil testing system of claim 4 wherein said variety of soil types includes sensitive, fine grained soils; organic soils; peats; and very stiff sands to clayey sands, each of said variety of soil types having a coefficient of permeability of $10^{-5}$ cm/sec.

6. The in soil testing system of claim 4 wherein said variety of soil types includes silt mixtures; clayey silts to silty clays; and very stiff, fine grained soils, each of said variety of soil types having a coefficient of permeability of $10^{-6}$ cm/sec.

7. The in soil testing system of claim 4 wherein said variety of soil types includes sand mixtures; and silty sands to sandy silts, each of said variety of soil types having a coefficient of permeability of $10^{-4}$ cm/sec.

8. The in-soil testing system of claim 4 wherein said variety of soil types includes clays to silty clays, each of said variety of soil types having a coefficient of permeability of $10^{-7}$ cm/sec.

9. The in soil testing system of claim 4 wherein said variety of soil types includes sands to clean sands to silty sands, each of said variety of soil types having a coefficient of permeability of $10^{-2}$ cm/sec.

10. The in soil testing system of claim 4 wherein said variety of soil types includes gravelly sands to sands, each of said variety of soil types having a coefficient of permeability of $10^{-1}$ cm/sec.

11. The in soil testing system of claim 1 further 27-t, comprising a printer connected to said digital computer, said printer providing a printout of the water depth below surface and the hydraulic conductivity for each of said plurality of depths of penetration of said probe.

12. A method for investigating soil parameters and collecting data and information relating thereto comprising:

positioning a probe located at one end of a string of steel pipes, on a soil surface, said probe including a plurality of sensors for measuring said soil parameters;

applying a force to the other end of said string of steel pipes to forcibly penetrate said probe into the soil below said soil surface at a constant penetration rate;

measuring pore water pressure in the soil with one of said sensors at a plurality of depths of penetration of said probe in said soil;

measuring forces resisting tip penetration by said probe with a second of said sensors at a plurality of depths of penetration of said probe in said soil;

measuring lateral forces resisting penetration by said probe with a third of said sensors at a plurality of is depths of penetration of said probe in said soil;

recording in digital form the analog output of all of said plurality of sensors of said probe in a repetitive manner while said probe is being penetrated into said soil;

processing said data and information relating to said soil parameters for each of said plurality of depths of penetration of said probe to generate a pressure dissipation curve for said pore water pressure in the soil at each of said plurality of depths of penetration of said probe and a hydrostatic pressure profile which illustrates a final pressure point for the pressure dissipation curve of each of said plurality of depths of penetration of said probe; and plotting a best fit line for the final pressure point of only completed pressure dissipation curves, said best fit line being used to determined a water depth below surface for the soil said probe is penetrating.

13. A method for investigating soil parameters and collecting data and information relating thereto comprising:

positioning a probe located at one end of a string of steel pipes, on a soil surface, said probe including a plurality of sensors for measuring said soil parameters;

applying a force to the other end of said string of steel pipes to forcibly penetrate said probe into the soil below said soil surface at a constant penetration rate;

measuring pore water pressure in the soil with one of said sensors at a plurality of depths of penetration of said probe in said soil;

measuring forces resisting tip penetration by said probe with a second of said sensors at a plurality of depths of penetration of said probe in said soil;

measuring lateral forces resisting penetration by said probe with a third of said sensors at a plurality of depths of penetration of said probe in said soil;

recording in digital form the analog output of all of said plurality of sensors of said probe in a repetitive manner while said probe is being penetrated into said soil;

processing said data and information relating to said soil parameters for each of said plurality of depths of penetration of said probe to generate a pressure dissipation curve for said pore water pressure in the soil at each of said plurality of depths of penetration of said probe and a hydrostatic pressure profile which illustrates a final pressure point for the pressure dissipation curve of each of said plurality of depths of penetration of said probe;

plotting a best fit line for the final pressure point of only completed pressure dissipation curves, said best fit line being used to determined a water depth below surface for the soil said probe is penetrating;

calculating a hydraulic conductivity for each of said plurality of depths of penetration of said probe whenever sufficient data exists to calculate said hydraulic conductivity; and generating a hydraulic conductivity profile which includes the hydraulic conductivity calculated for each of said plurality of depths of penetration of said probe.

\* \* \* \* \*

UNITED STATES PATENT AND TRADEMARK OFFICE
CERTIFICATE OF CORRECTION

PATENT NO.    : 6,208,940 B1  
DATED         : March 27, 2001  
INVENTOR(S)   : Welssman et al.

It is certified that error appears in the above-identified patent and that said Letters Patent is hereby corrected as shown below:

<u>Title page,</u>  
Item [73], Assignee, should include the following:  
-- Toyota Motor Corporation, Shizuoka (JP) --; and -- Toyota Central Research and Development Laboratories, Inc., Aichi (JP) --.

Signed and Sealed this

Eighteenth Day of May, 2004

JON W. DUDAS  
*Acting Director of the United States Patent and Trademark Office*

UNITED STATES PATENT AND TRADEMARK OFFICE
CERTIFICATE OF CORRECTION

PATENT NO.   : 6,208,940 B1
DATED        : March 27, 2001
INVENTOR(S)  : Mark L. Kram et al.

It is certified that error appears in the above-identified patent and that said Letters Patent is hereby corrected as shown below:

This certificate supersedes Certificate of Correction issed May 18, 2004, the number was erroneously mentioned and should be vacated since no Certificate of Correction was granted.

Signed and Sealed this

Twenty-ninth Day of June, 2004

JON W. DUDAS
*Acting Director of the United States Patent and Trademark Office*